(12) United States Patent
Hess et al.

(10) Patent No.: US 8,303,599 B2
(45) Date of Patent: Nov. 6, 2012

(54) SYRINGE

(75) Inventors: Brian Hess, Charlestown, MA (US);
Matthew E. Murphy, Pembrokestown (IE)

(73) Assignee: Stryker Leibinger GmbH & Co. KG (DE)

( * ) Notice: Subject to any disclaimer, the term of this patent is extended or adjusted under 35 U.S.C. 154(b) by 0 days.

(21) Appl. No.: 12/887,663

(22) Filed: Sep. 22, 2010

(65) Prior Publication Data

US 2011/0015640 A1    Jan. 20, 2011

Related U.S. Application Data

(63) Continuation of application No. 11/641,618, filed on Dec. 19, 2006, which is a continuation-in-part of application No. 11/522,224, filed on Sep. 15, 2006, now abandoned, and a continuation-in-part of application No. 11/343,183, filed on Jan. 30, 2006, now abandoned.

(51) Int. Cl.
*A61B 17/56* (2006.01)
*B65D 83/10* (2006.01)
*B65D 25/08* (2006.01)

(52) U.S. Cl. ........... 606/92; 206/219; 206/364; 206/571

(58) Field of Classification Search .............. 606/92–94; 604/6.12, 187; 206/219, 364, 365, 571
See application file for complete search history.

(56) References Cited

U.S. PATENT DOCUMENTS

| | | | |
|---|---|---|---|
| 3,083,821 A | 4/1963 | Woodson |
| 3,618,751 A | 11/1971 | Rich |
| 3,756,571 A | 9/1973 | Winberg et al. |
| 4,008,803 A | 2/1977 | Smith et al. |
| 4,135,868 A | 1/1979 | Schainholz |
| 4,277,184 A | 7/1981 | Solomon |
| 4,294,349 A | 10/1981 | Ibsen et al. |
| 4,299,238 A | 11/1981 | Baidwan et al. |
| 4,341,302 A | 7/1982 | Baker et al. |

(Continued)

FOREIGN PATENT DOCUMENTS

CN    2553815 Y    6/2003

(Continued)

OTHER PUBLICATIONS

Office Action from Corresponding Japanese Application No. 2007-19711, dated Jul. 20, 2010.

(Continued)

*Primary Examiner* — Ellen C Hammond

(74) *Attorney, Agent, or Firm* — Lerner, David, Littenberg, Krumholz & Mentlik, LLP

(57) ABSTRACT

A stand for use with a syringe is structured to engage a portion of the syringe in order to maintain the syringe in an upright position. The stand may include an aperture structured to engage the nozzle or the plunger of the syringe. Another embodiment of the stand may include a protrusion structured to engage the proximal end of the syringe, or a clip structured to engage a handle of the syringe. The stand may include a package portion having compartments for holding various components, such as components of a bone cement preparation kit. The proximal and distal portions of the barrel of the syringe may be separable to provide an opening into the barrel through which an injectable material may be inserted. The plunger of the syringe may also include a plunger rod removably affixed to the plunger tip.

18 Claims, 14 Drawing Sheets

U.S. PATENT DOCUMENTS

| | | | |
|---|---|---|---|
| 4,364,473 A | 12/1982 | Bogaert et al. | |
| 4,420,085 A | 12/1983 | Wilson et al. | |
| D280,290 S | 8/1985 | Bakus | |
| 4,632,672 A | 12/1986 | Kvitrud | |
| 4,671,263 A | 6/1987 | Draenert et al. | |
| 4,673,085 A | 6/1987 | Badouard et al. | |
| 4,697,703 A | 10/1987 | Will | |
| 4,701,165 A * | 10/1987 | DeHaitre | 604/228 |
| 4,820,306 A | 4/1989 | Gorman et al. | |
| 4,832,692 A | 5/1989 | Box et al. | |
| 4,838,866 A | 6/1989 | Marshall, Sr. | |
| 4,844,249 A | 7/1989 | Coulombe et al. | |
| 4,844,251 A | 7/1989 | Gueret et al. | |
| 4,865,591 A | 9/1989 | Sams et al. | |
| 4,880,610 A | 11/1989 | Constantz | |
| 4,966,601 A | 10/1990 | Draenert et al. | |
| 4,973,168 A | 11/1990 | Chan et al. | |
| 5,007,535 A | 4/1991 | Meseke et al. | |
| 5,047,031 A | 9/1991 | Constantz | |
| 5,102,083 A * | 4/1992 | Baskas | 248/223.41 |
| 5,121,779 A * | 6/1992 | Green | 141/337 |
| 5,129,905 A | 7/1992 | Constantz | |
| 5,178,845 A | 1/1993 | Constantz et al. | |
| 5,193,672 A * | 3/1993 | Long | 206/45.2 |
| 5,203,459 A | 4/1993 | Wade | |
| 5,238,003 A | 8/1993 | Baidwan et al. | |
| 5,240,415 A | 8/1993 | Haynie | |
| 5,265,724 A | 11/1993 | Dondlinger | |
| 5,333,737 A | 8/1994 | Clark | |
| 5,334,173 A | 8/1994 | Armstrong, Jr. | |
| 5,336,264 A | 8/1994 | Constanz et al. | |
| 5,462,356 A | 10/1995 | Murray | |
| 5,514,137 A | 5/1996 | Coutts | |
| 5,569,442 A | 10/1996 | Fulmer et al. | |
| 5,586,821 A | 12/1996 | Bonitati et al. | |
| 5,624,184 A | 4/1997 | Chan | |
| 5,697,981 A | 12/1997 | Ison et al. | |
| 5,709,742 A | 1/1998 | Fulmer et al. | |
| 5,735,825 A | 4/1998 | Stevens et al. | |
| 5,782,971 A | 7/1998 | Constantz et al. | |
| 5,794,904 A | 8/1998 | Hackley | |
| 5,820,632 A | 10/1998 | Constantz et al. | |
| 5,823,363 A | 10/1998 | Cassel | |
| 5,842,785 A | 12/1998 | Brown et al. | |
| 5,865,803 A | 2/1999 | Major | |
| 5,900,254 A | 5/1999 | Constantz | |
| 5,951,160 A | 9/1999 | Ronk | |
| 5,952,010 A | 9/1999 | Constantz | |
| 5,962,028 A | 10/1999 | Constantz | |
| 5,968,253 A | 10/1999 | Poser et al. | |
| 5,975,295 A | 11/1999 | Diamond | |
| 5,975,305 A | 11/1999 | Barger | |
| 6,002,065 A | 12/1999 | Constantz et al. | |
| 6,005,162 A | 12/1999 | Constantz | |
| D422,674 S * | 4/2000 | Chrisco et al. | D23/200 |
| 6,083,229 A | 7/2000 | Constantz et al. | |
| 6,120,481 A * | 9/2000 | Rennert et al. | 604/187 |
| 6,241,734 B1 | 6/2001 | Scribner et al. | |
| 6,257,408 B1 | 7/2001 | Odierno | |
| 6,273,916 B1 | 8/2001 | Murphy | |
| 6,312,258 B1 | 11/2001 | Ashman | |
| 6,348,055 B1 | 2/2002 | Preissman | |
| 6,364,519 B1 | 4/2002 | Hughes et al. | |
| 6,382,575 B1 | 5/2002 | Frush et al. | |
| 6,383,190 B1 | 5/2002 | Preissman | |
| 6,409,972 B1 | 6/2002 | Chan | |
| RE37,776 E * | 7/2002 | Foltz | 220/86.2 |
| 6,450,993 B1 | 9/2002 | Lin | |
| 6,458,147 B1 | 10/2002 | Cruise et al. | |
| 6,511,457 B2 | 1/2003 | Thompson | |
| 6,511,459 B1 | 1/2003 | Fago | |
| 6,516,977 B2 | 2/2003 | Chan | |
| 6,588,587 B2 | 7/2003 | Johnson et al. | |
| 6,592,247 B1 | 7/2003 | Brown et al. | |
| D479,329 S | 9/2003 | Sanguinetti | |
| D499,180 S * | 11/2004 | Best | D24/122 |
| D499,616 S * | 12/2004 | Sanders et al. | D7/700 |
| 6,916,308 B2 | 7/2005 | Dixon et al. | |
| 6,957,909 B1 | 10/2005 | Dingeldein et al. | |
| 7,022,112 B2 | 4/2006 | Pokorney | |
| 7,160,020 B2 | 1/2007 | Sand | |
| 7,278,778 B2 | 10/2007 | Sand | |
| 7,308,985 B2 | 12/2007 | Riley | |
| 2002/0185406 A1 | 12/2002 | Massengale et al. | |
| 2002/0191487 A1 | 12/2002 | Sand | |
| 2003/0191453 A1 | 10/2003 | Velez et al. | |
| 2004/0195131 A1 | 10/2004 | Spolidoro | |
| 2004/0215143 A1 | 10/2004 | Brady et al. | |
| 2004/0215202 A1 | 10/2004 | Preissman | |
| 2004/0238391 A1 | 12/2004 | Pond | |
| 2004/0254538 A1 * | 12/2004 | Murphy et al. | 604/181 |
| 2005/0033231 A1 | 2/2005 | Powell | |
| 2005/0077225 A1 | 4/2005 | Usher et al. | |
| 2005/0113843 A1 | 5/2005 | Arramon | |
| 2005/0241965 A1 | 11/2005 | Kurc | |
| 2006/0187747 A1 | 8/2006 | Sand | |
| 2007/0121422 A1 | 5/2007 | Sand | |
| 2007/0225654 A1 | 9/2007 | Hess et al. | |
| 2008/0033447 A1 | 2/2008 | Sand | |

FOREIGN PATENT DOCUMENTS

| | | |
|---|---|---|
| EP | 361139 | 4/1990 |
| EP | 790063 | 8/1997 |
| JP | 2000-325362 A | 11/2000 |
| WO | 9006784 | 6/1990 |

OTHER PUBLICATIONS

Office Action from Corresponding Chinese Application No. 2007100027926, dated Feb. 23, 2011.

Office Action from Corresponding Japanese Application No. 2007-19711, dated Apr. 26, 2011.

Office Action from Corresponding Chinese Application No. 2007100027926, dated Nov. 27, 2009.

Office Action from U.S. Appl. No. 11/343,183, mailed Feb. 27, 2009.

Office Action from U.S. Appl. No. 11/522,224 mailed Apr. 9, 2010.

Office Action from U.S. Appl. No. 11/522,224, mailed Jun. 26, 2008.

* cited by examiner

A-A

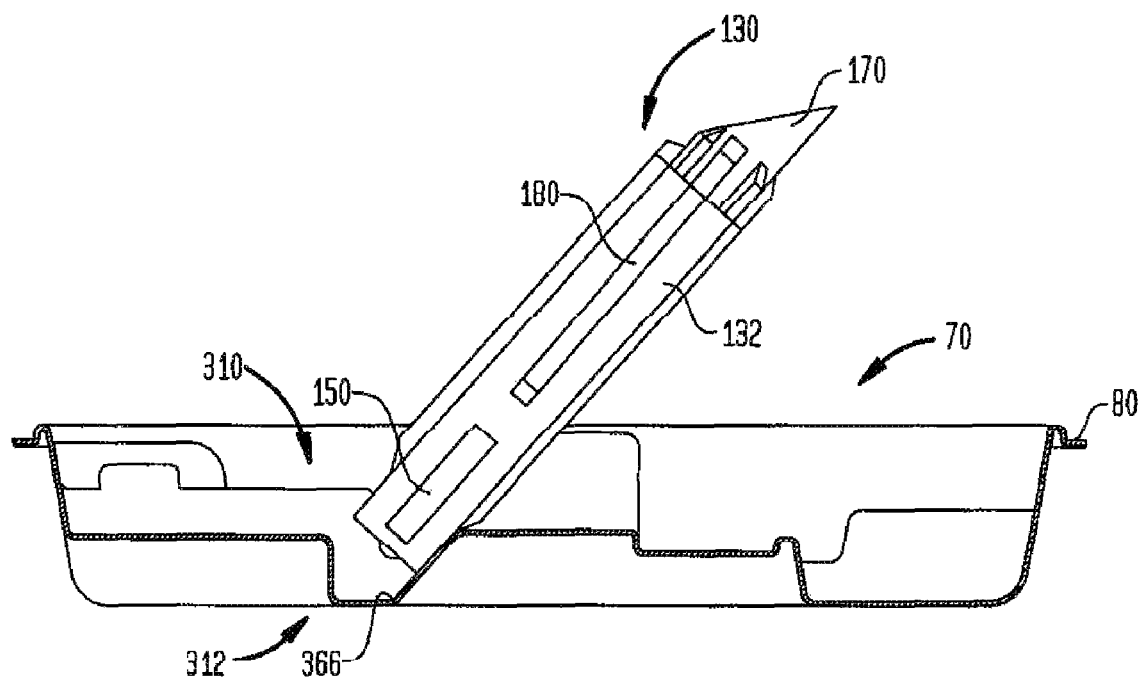

SYRINGE

CROSS-REFERENCE TO RELATED APPLICATIONS

This application is a continuation of U.S. application Ser. No. 11/641,618, filed on Dec. 19, 2006, which is a continuation-in-part of U.S. application Ser. No. 11/522,224, filed on Sep. 15, 2006, now abandoned, and application Ser. No. 11/343,183, filed on Jan. 30, 2006, now abandoned, the disclosures of which are incorporated herein by reference.

BACKGROUND OF THE INVENTION

The present invention relates to syringes and syringe stands and packages used in the medical field, with particular application in the orthopedic field. Many orthopedic procedures require the use of any one of various types of bone cement compositions. Such compositions aid both in the setting of bone and in securing implants or other devices to bone during orthopedic procedures. Advances in bone cement compositions have led to rapid setting bone cement compositions, which are advantageous because they shorten the time required both for surgery and the time needed for recovery after surgery. Some forms of bone cement compositions are heat-activated. Heat-activated bone cement compositions are caused to set into solid form by exposure to a heat source. Particularly, heat activated bone cement compositions are ideal because they set in response to body heat provided by the host into which they are deposited. Furthermore, some procedures require that such compositions are injected using a syringe.

Certain problems arise when preparing to inject a bone cement composition into a host using a syringe. Particularly, problems arise when attempting to transfer the cement composition from a mixing apparatus into the syringe. Various solutions have been proposed to solve this problem, which may require the use of complicated pumps and tubes to mix or transfer the cement composition. Furthermore, no apparatus has been proposed which allows a user to transfer the cement composition into the syringe without holding the syringe. This presents a problem, in particular, with use of a heat-activated bone cement composition, because the heat from a user's hand will raise the temperature of the syringe and cause the bone cement composition therein to set, becoming a solid mass contained within the syringe that is no longer useable. Therefore, it is ideal to provide an apparatus that aids in the transfer of the bone cement composition into the syringe without requiring the user thereof to physically hold the syringe.

SUMMARY OF THE INVENTION

The present invention relates to a stand for use with a syringe having a feature, the stand having a base portion, and a top portion. The top portion has an aperture formed therein, the aperture being structured to engage a feature of the syringe. The top portion is positioned relative to the base portion such that the syringe is maintained in an upright position when the feature of the syringe is engaged within the aperture. In order to better engage the feature of the syringe, a preferred embodiment of the aperture includes a series of projections and recesses configured to form a pressure-fit with the feature.

A particular embodiment of the present invention includes a stand for use with a syringe having a barrel and a nozzle, the stand having a base portion, and a top portion. The top portion has an aperture formed therein, the aperture being structured to engage the nozzle of the syringe. The top portion is positioned relative to said base portion such that the syringe is maintained in an upright position when the nozzle of the syringe is engaged within said aperture.

An alternative embodiment of the present invention includes a stand for use with a syringe having a plunger with a proximal end, the stand having a base portion, and a top portion. The top portion has an aperture formed therein, the aperture being structured to engage the proximal end of the plunger of the syringe. The top portion is positioned relative to the base portion such that the syringe is maintained in an upright position when the proximal end is engaged within the aperture.

In a further embodiment of the present invention, a stand according to one embodiment of the present invention further includes a package portion affixed to the stand at the base thereof. The package portion includes a compartment, preferably in the form of snap channel, wherein the compartment is adapted to hold the syringe within the package in a substantially horizontal position, particularly during shipping and storage of the syringe within the package. This embodiment can further include additional compartments within package portion for other components that are relevant to bone cement preparation such as containers for bone cement ingredients, mixing devices and attachments for the syringe.

A further embodiment of the present invention includes stand for use with a syringe having a proximal end and a distal end. The stand includes a base and a protrusion extending from the base. The protrusion is adapted to engage the proximal end of the syringe so as to maintain the syringe in a position such that the distal end of the syringe has a vertical position above a vertical position of the proximal end. The protrusion may be structured so as to extend into the proximal end of the syringe and/or form a pressure fit within the syringe.

The stand of the present embodiment may include a support that contacts a portion of the syringe located between the proximal and distal ends thereof so as to maintain a position of the syringe. The syringe may include a first handle and a second handle projecting outwardly from the barrel and positioned between the proximal and distal ends of the syringe, and the support may contact the first and second handles. Preferably, the handles of the syringe each include an interior surface and the support includes a first pedestal and a second pedestal. In such an embodiment, each of the first and second pedestals are positioned and shaped so as to project at least partially into the first and second handles, respectively. Additionally, the first and second pedestals may respectively include a first surface and a second surface arranged so as to contact a portion of the interior surfaces the respective handles.

Preferably, a stand according to the present embodiment is structured so that a longitudinal axis of the syringe is maintained at an angle relative to a surface on which the stand is positioned. In a preferred embodiment, the angle is between about 40 and 70 degrees, and preferably about 45 degrees.

An alternative aspect of the present invention relates to a stand for use with a syringe, including a base and a clip affixed to the base. The clip engages a portion of the syringe so as to removably secure the syringe to the stand in a position such that the distal end of the syringe is spaced vertically away from the base. Preferably, the syringe includes a handle extending outwardly from a barrel of the syringe, and the feature which the clip engages includes the handle of the syringe.

In a further embodiment, the clip includes a first surface and a second surface substantially parallel to each other. The first and second surfaces face each other and are spaced apart such that the first surface contacts a first area of the handle and the second surface contacts a second area of the handle. The first and second areas of the handle being on opposing sides of the handle. Preferably, the base of the stand further includes a surface for contacting a portion of the barrel of the syringe near the proximal end thereof so as to contribute to a pressure-fit between the clip and the handle of the syringe. Further preferably, the second surface of the clip includes a projection extending therefrom so as to contact a third area of the handle of the syringe.

A further alternative aspect of the present invention relates to a stand for use with a syringe, including a base and a support structure affixed to the base and structured to engage a portion of the syringe so as to removably secure the syringe to the stand such that a distal end of the syringe is spaced vertically away from the base.

The present invention also includes a method of preparing a syringe to deliver a material, the method including the steps of: providing a syringe; providing a stand having an aperture capable of engaging a feature of the syringe, wherein the stand is capable of maintaining the syringe in an upright position; inserting the feature of the syringe within the aperture such that the syringe is maintained in an upright position; and depositing an amount of a material into the syringe.

The present invention further includes an alternative method of preparing a syringe to deliver a material. The method includes the step of providing a syringe having a proximal end and a distal end and a barrel extending between the proximal and distal ends, the barrel having an interior cavity for receiving a material. The method also includes providing a stand including a protrusion extending from a base, and positioning the syringe on the stand such that the protrusion engages the proximal end of the syringe so as to maintain the syringe in a position such that the distal end of the syringe has a vertical position above a vertical position of the proximal end.

The stand of the present method may further include a support affixed to the base thereof. The step of positioning the syringe including positioning a portion of the barrel so as to rest against the support. Further, the barrel of the syringe of the present invention may include a first handle having an interior surface and a second handle having an interior surface, the first and second handles projecting from the barrel. Additionally, the support of the stand of the present method may include a first pedestal having a top surface thereof and a second pedestal having a top surface thereof. The step of positioning such a syringe on such a stand may include placing a portion of the interior surface of the first handle in contact with the top surface of the first pedestal and placing a portion of the interior surface of the second handle in contact with the top surface of the second pedestal.

An alternative method of preparing a syringe to deliver a material includes placing a stand on a surface, the stand having a base adapted for stable resting on the surface and having a support structure adapted to engage a portion of the syringe. The method further includes engaging a portion of the syringe with the support structure so as to removably secure the syringe to the stand in a position such that distal end of the syringe is spaced vertically away from the base. The syringe may include a handle extending outwardly from a barrel thereof, the support structure may include a clip affixed to the base, and the step of engaging a portion of the syringe with the clip may include assembling the handle with the clip.

In a preferred embodiment, the syringe includes a barrel extending between the distal end and a proximal end, and the position of ht syringe is further such that the proximal end of the syringe is positioned adjacent to the base of the stand and the barrel extends away from the base at an angle relative to the surface. The angle is preferably between 30 and 90 degrees and, more preferably, the angle is approximately 45 degrees.

The present invention also includes a kit having therein a syringe, components used in forming an injectable bone cement composition, and a container used in mixing the bone cement components. The kit of the present invention can further include a stand including a base portion and a top portion. The top portion of the stand has an aperture formed therein, the aperture being structured to engage a feature of the syringe. The top portion is positioned relative to the base portion such that the syringe is maintained in an upright position when the feature of the syringe is engaged within the aperture. The stand can further include a package portion for containing the other components for the kit. In a further embodiment, the kit includes a desiccant to prevent aging of the components used in forming the bone cement composition, particularly those which may be in the form of a powder, and more particularly, those powders which may be more susceptible than others to moisture.

Alternatively, a kit according to an embodiment of the present includes a syringe for delivering a material. The syringe includes a barrel having a proximal end and a distal end and a plunger tip slideably engaged within the barrel so as to form a seal between an interior wall of the barrel and an outer periphery of the plunger tip. The kit of the present embodiment also includes a stand having a base and a protrusion extending from the base. The protrusion is adapted to engage the proximal end of the syringe, the plunger tip being positioned within the barrel, so as to maintain the syringe in a position such that the distal end of the syringe has a vertical position above a vertical position of the proximal end.

An alternative embodiment of the present invention relates to a kit including a syringe and a stand. The syringe has a barrel extending between a proximal end and a distal end thereof. The stand includes a base and a clip affixed to the base. The clip is adapted to engage a portion of the syringe so as to removably secure the syringe to the stand in a position such that the distal end of the syringe is spaced vertically away from the base. The kit may further include a package portion, which may include a compartment for removably holding the syringe therein.

The present invention further includes a syringe for use with a stand, the syringe having a barrel, a nozzle, and a plunger. The barrel is divided into a proximal portion and a distal portion, the proximal portion and distal portions being separable to provide an opening into the barrel of the syringe.

A further embodiment of the present invention includes syringe for delivering a material. The syringe of this embodiment includes a barrel having a proximal end and a distal end, and a plunger tip slideably engaged within the barrel so as to form a seal between an interior wall of the barrel and an outer periphery of the plunger tip. A plunger rod is removably affixed to the plunger tip portion such that the plunger rod can be attached and detached from the plunger tip while the plunger tip is slideably engaged within the barrel.

The syringe of the present embodiment may be such that the distal end forms an opening for access to the barrel, the opening having a diameter substantially equal to a diameter of the barrel. The syringe may further include a nozzle capable of being removably affixed to the distal end of the opening, the nozzle having an opening with a diameter smaller than a diameter of the barrel. Alternatively, the syringe of the present embodiment may include a funnel capable of being removably affixed to the distal end of the barrel, the funnel having an opening with an area at least as large as an area of the opening of the barrel.

Dependently of the foregoing or in connection therewith, the syringe of the present invention may include a barrel having an outer periphery including a plurality of ribs extending outwardly therefrom for the purpose of counteracting the heat from a user's hand and its potential effect on a fast-setting bone cement or other adhesive or compound utilized in the syringe.

BRIEF DESCRIPTION OF THE DRAWINGS

The present invention will be better understood on reading the following detailed description of nonlimiting embodiments thereof, and on examining the accompanying drawings, in which:

FIG. 14 is a cross-sectional view of the stand shown in FIG. 12 taken along line B-B with a syringe, show in full sectional view, assembled therewith.

DETAILED DESCRIPTION

In describing the preferred embodiments of the subject matter illustrated and to be described with respect to the drawings, specific terminology will be resorted to for the sake of clarity. However, the invention is not intended to be limited to the specific terms so selected, and is to be understood that each specific term includes all technical equivalents which operate in a similar manner to accomplish a similar purpose.

Figure 1:
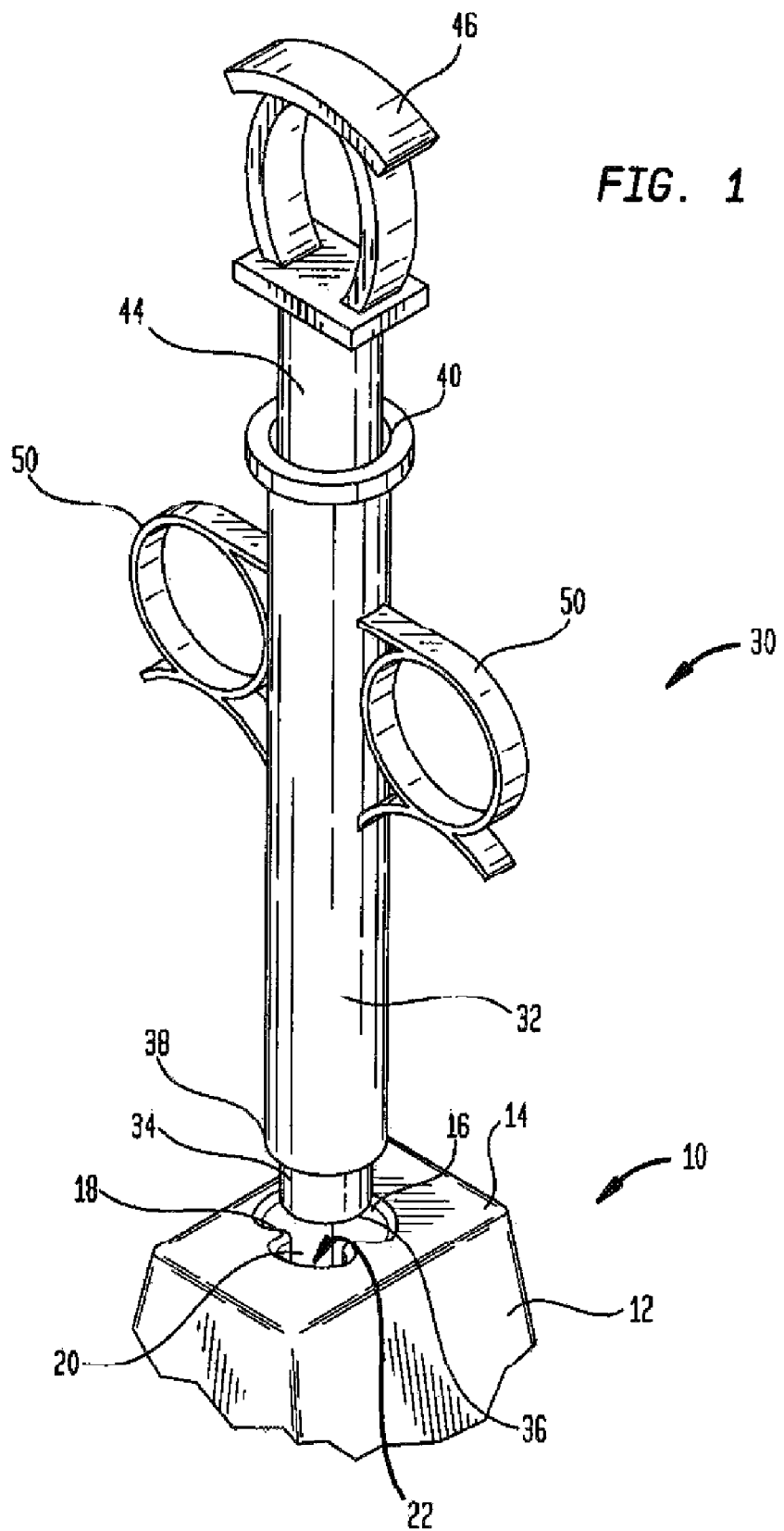
FIG. 1 is a perspective view of a syringe and a stand according to an embodiment of the present invention.
Figure 2:
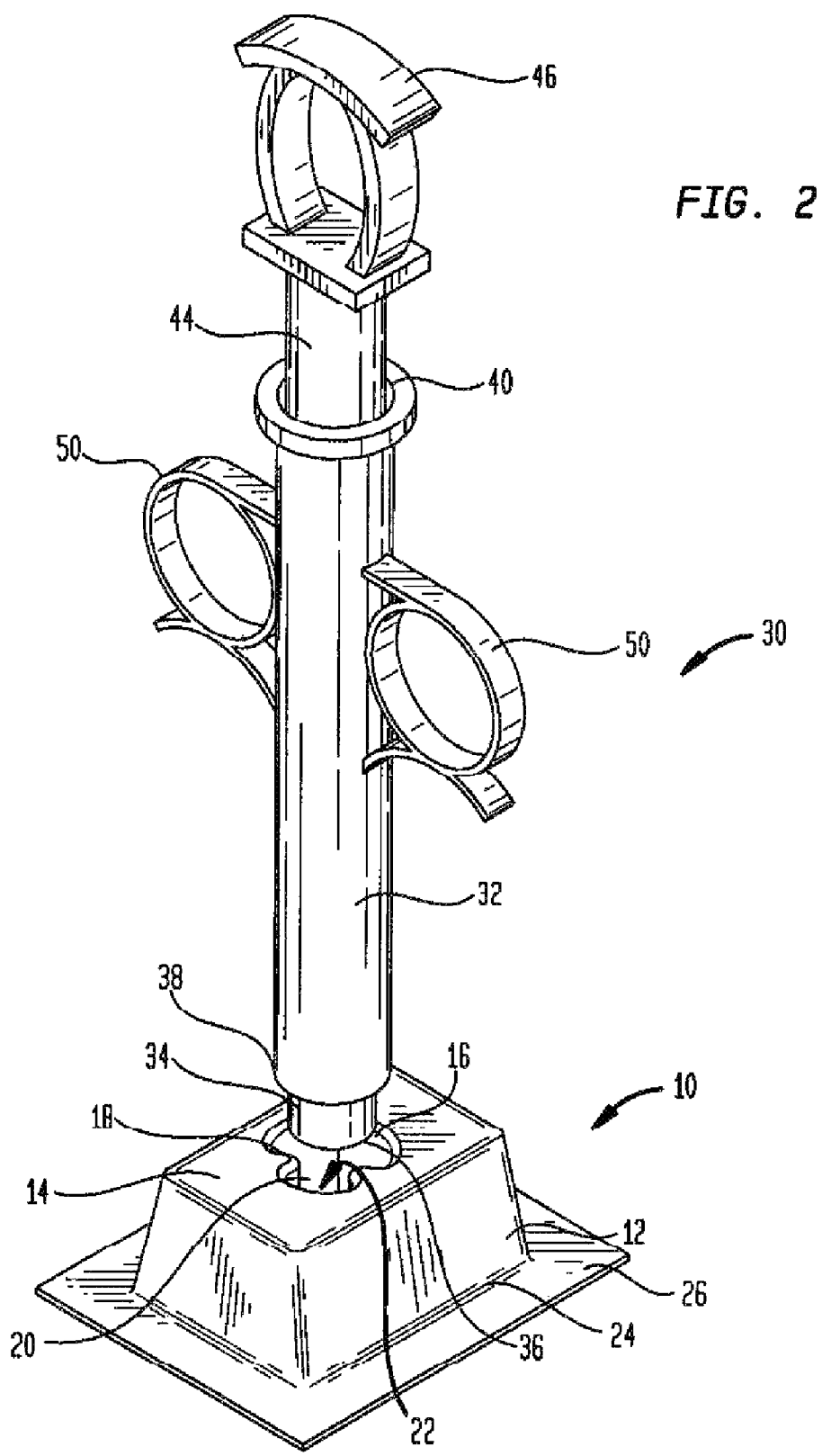
FIG. 2 is a perspective view of a syringe and a stand according to a further embodiment of the present invention.

Referring to the drawings, wherein like reference numerals represent like elements, there is shown in FIG. 1, in accordance with one embodiment of the present invention, a syringe stand designated generally by reference numeral 10. In a preferred embodiment, stand 10 includes base portion 12 and top portion 14. Although the shape of base 12 as shown in FIG. 1 is substantially rectangular, base 12 does not require the use of any particular shape; however, base 12 should be structured to allow stand 10 to stably rest on a surface while in use. As shown in FIG. 2, base 12 can include a flat bottom portion 24 that is sufficiently wide enough to stably support syringe 30 during use. Preferably, the flat bottom portion 24 includes a flange 26 formed thereon. In a further preferred embodiment, shown in FIG. 4-6, stand 10 includes a package portion 70 that is preferably attached to base 12. The package portion is useful for transporting and storing with syringe 30, other tools or materials that are used in connection with syringe 30.

Stand 10 is preferably made of plastic or any other suitable polymeric material such as polyethylene, and is preferably transparent. The thickness and composition of the material used to form stand 10 should result in stand 10 being flexible. Preferably, stand 10 is formed by vacuum molding or other similar methods. Preferably, stand 10 is in the form of a blister pack such that it is formed from a thin, unitary piece of material that is molded to form the three-dimensional shape of stand 10. This results in the stand 10 having a generally hollow inside portion (not shown). The material comprising stand 10 should be thin enough to be flexible, but should be thick enough to be rigid such that it securely engages an appropriate feature of syringe 30. Such a feature can include barrel 32, including any section thereof, or handles 50, which are affixed to barrel 32, but will preferably include nozzle 34 or proximal end 46 of plunger 44.

In one embodiment of the invention, top portion 14 of stand 10 is generally planar, except for aperture 16 formed therein. Aperture 16 is structured and dimensioned to receive nozzle 34 of syringe 30 and can take a variety of shapes from circular to more complicated geometric designs. Generally, the dimension of aperture 16 should be such that it forms a pressure fit with nozzle 34. For example, if nozzle 34 is substantially circular, aperture 16 can also be circular, having a diameter that is slightly less than that of nozzle 34.

The pressure fit formed between aperture 16 and nozzle 34 should be sufficient to hold syringe 30 in an upright position when inserted in the stand. For purposes of this invention, upright is not limited to a completely vertical position (i.e., orthogonal to the surface on which stand 10 rests), but includes any orientation of syringe 30 wherein the opening through which the injectable material 88 is deposited into syringe 30 has an elevation that is vertically greater than that of the portion of syringe 30 which is inserted into the stand.

Syringe 30 can vary in size, depending on the application for which it is designed. Accordingly, aperture 16 will be dimensioned to fit a specific one of these various sizes. Ideally, syringe 30 will be packaged with stand 10 having an aperture 16 of an appropriate size to match that of nozzle 34 of syringe 30. In a preferred embodiment, stand 10 is integrally formed with part of packaging 70 for syringe 30.

In a preferred embodiment, aperture 16 has a bottom portion 22 that is positioned below top portion 14 at a distance such that shoulder section 38 of syringe 30 contacts top portion 14 and port 36 of nozzle 34 contacts bottom surface 22 of aperture 16. Such an arrangement will prevent the material that is placed within syringe 30 from leaking out of nozzle 34 while syringe 30 is held upright within stand 10.

Figure 5:
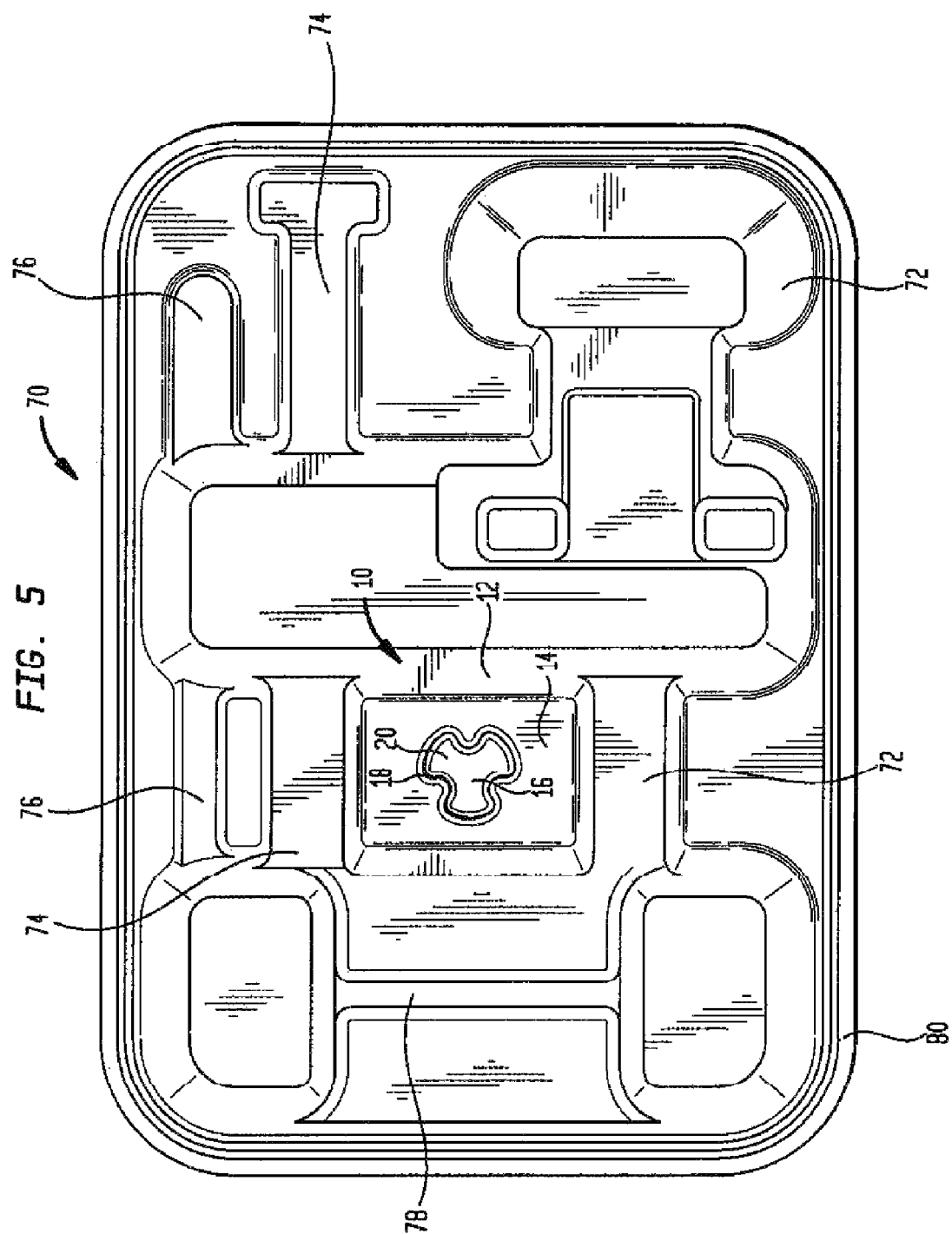
FIG. 5 is a top view of a stand according to an embodiment of the present invention.

As shown in FIG. 5, a preferred embodiment of stand 10 includes an aperture 16 having a shape that forms a series of projections 18 and accompanying recesses 20. Any number of projections 18 and recesses 20 can be used in the shape of aperture 16, but preferably aperture 16 has at least three projections 18 and three recesses 20. In such an arrangement, projections 18 make contact with nozzle 34, while recesses 20 are spaced apart therefrom. Projections 18 are dimensioned to form a pressure fit with nozzle 34. In one embodiment, aperture 16 has one projection 18 and one recess 20, wherein nozzle 34 makes contact with a portion of recess 20 and with projection 18. In a preferred embodiment, aperture 16 is tapered, having a greater diameter toward the top portion 14 than toward the bottom 22 thereof.

Figure 3:
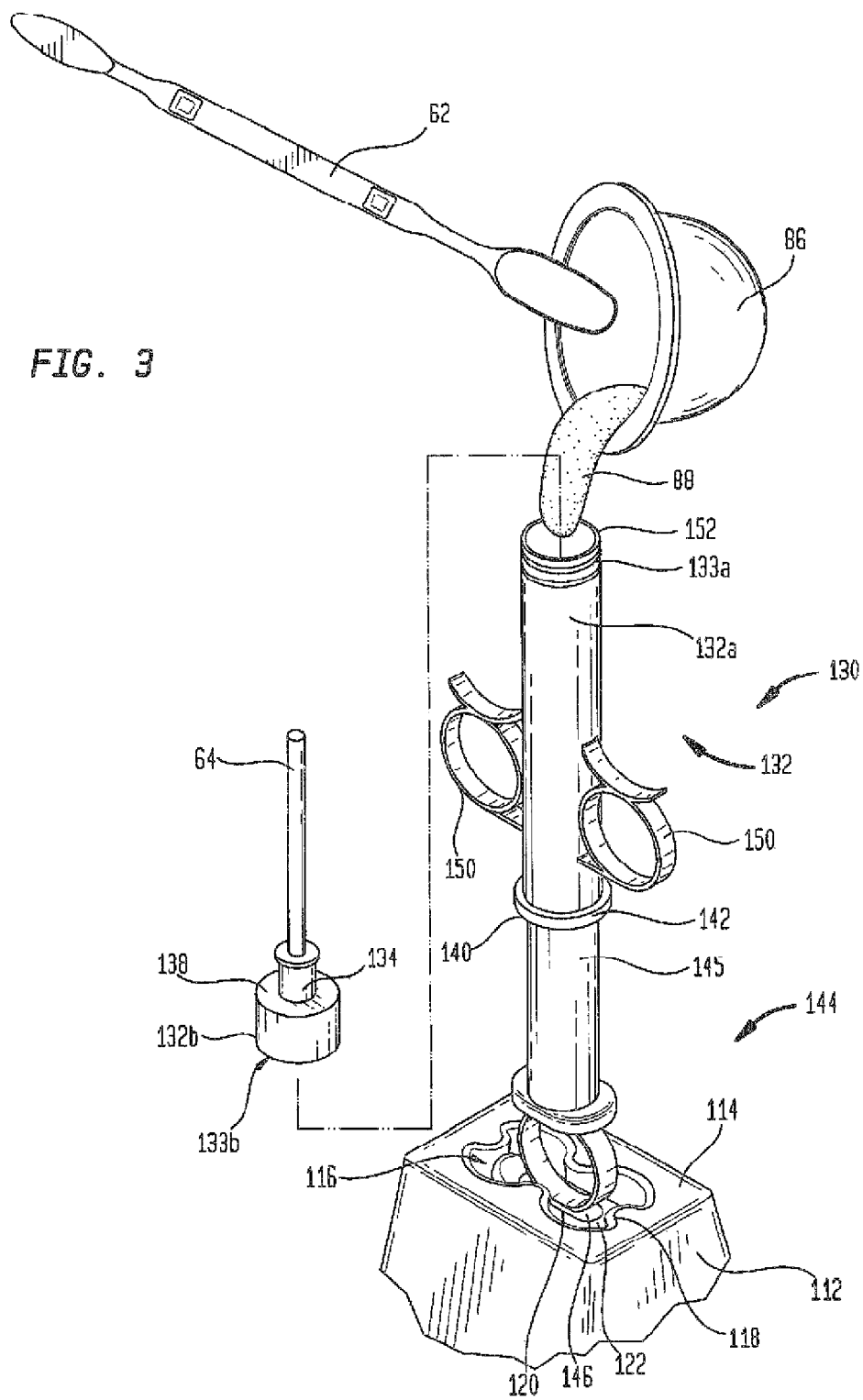
FIG. 3 is a perspective assembly view of a syringe and a stand according to an alternative embodiment of the present invention during a step in a method of use thereof.

Referring now to FIG. 3, in an alternative embodiment of the present invention, aperture 116 is adapted to engage the proximal end 146 of plunger 144. Plunger 144 is of the type normally used in connection with a syringe. Specifically, plunger 144 is cylindrical in shape and is dimensioned to fit within the open end 140 of syringe 130. Plunger 144 typically includes a tip (such as tip 48 shown in FIG. 4) which effects a seal between the inside of the barrel 132 of syringe 130. The seal between the tip and barrel 132 is preferably impervious to fluid. Furthermore, the seal formed between the tip and barrel 132 provides a friction force therebetween, which is sufficient to support the weight of barrel 132 when syringe 130 is secured in stand 110. Such an arrangement eliminates the need present in other embodiments of stand 10 to structure aperture 16 to form a seal over the open end of nozzle 34. Furthermore, the present embodiment facilitates the removal of air pockets or bubbles that may be present in the injectable composition when it is transferred into syringe 130.

Proximal end 146 of plunger 144 varies in shape among differing plunger designs, but will typically form a surface that is larger in area than plunger rod 145. Aperture 116 can be adapted to receive any feature which may be present on the proximal end 146 of plunger 144. Aperture 116 can be of any shape that will provide a pressure-fit sufficient to engage proximal end 146 to maintain the syringe in an upright position. In its most simple form, aperture 116 will have a profile along a horizontal plane therethrough that substantially matches the profile of proximal end 146 when intersected by the same plane. Preferably, aperture 116 is tapered such that it is wider near the top surface 114 than at the bottom 122 of the aperture 116. This arrangement aids in inserting proximal end 146 into the aperture 116.

In a preferred embodiment, aperture 116 includes a series of projections 118 and recesses 120 designed to contact proximal end 146 at a predetermined number of points. Although any number of projections 118 and recesses 120 may be employed in such a design, it is preferable that the aperture has four projections and four recesses. The overall size of aperture 116, as well as the projections 118 and recesses 120 will vary in accordance with the shape of proximal end 146 in a manner that can be determined by those having reasonable skill in the art.

Syringe 130 of the type depicted in FIG. 3 is particularly advantageous for use with a stand of the present embodiment and, perhaps, for other purposes. This variation of syringe 130 has a two-part barrel construction, wherein barrel 132 is divided into proximal and distal portions 132a, 132b. Distal portion 132b of barrel 132 includes nozzle 134, and proximal portion 132a includes open end 140 and handles 150. Proximal and distal portions 132a, 132b of barrel 132 are designed for mutual engagement therebetween and preferably include a mechanism, such as a thread-fit, pressure-fit or snap fit, to secure the engagement between the two portions 132a, 132b. As shown in FIG. 3, this mechanism preferably includes mating threaded sections 133a, 133b, one on each of proximal portion 132a and distal portion 132b. Preferably, the male portion 133a of the threaded section 133 is included on proximal portion 132a of barrel 132, and female threaded portion 133b is included on distal portion 132b.

This variation of syringe 130 operates with stand 110 by providing a sufficiently wide opening 152 to deposit the injectable substance 88 into barrel 132. In operation, proximal end 146 of plunger 144 is inserted into aperture 116 of stand 110, the distal portion 132b of barrel 132 having been removed from the proximal portion 132a. The tip of plunger 144 is positioned sufficiently near the opening end 140 to allow syringe 130 to contain the desired amount of injectable substance 88. The position of the tip within barrel 132 is maintained by the friction between the tip and the interior of barrel 132. The injectable substance 88 is then prepared and deposited into the syringe through opening 152. Then, distal portion 132b of barrel 132 is re-assembled onto proximal portion 132a of barrel 132 and syringe 130 is used in a typical fashion.

It is preferable that proximal portion 132a of barrel 132 represents a greater portion of the entire barrel 132 than does distal portion 132b; but the barrel may be divided anywhere, depending on the purpose for which it is divided. For filling the proximal portion 132a, the distal portion 132b need only be large enough as necessary to support nozzle 134. This arrangement allows the interior of barrel 132 to be filled with as much of injectable substance 88 as possible before distal portion 132b is re-assembled onto proximal portion 132b. This arrangement is also advantageous for a kit having several choices of different nozzle assemblies that can be fit onto the proximal portion 132a. Preferably, such different nozzles could be differently sized for different applications and a surgeon could choose a nozzle intraoperatively. Most preferably, when connecting the portions 132a and 132b opening 152 abuts the inside surface of shoulder section 138 of distal portion 132b when distal portion 132b is engaged onto proximal portion 132a.

In an alternative form of the invention, a recess can be provided in the package which is larger than the feature of the syringe to be held therein (whether it be the nozzle or the proximal plunger portion), as well as deeper so that the syringe can be placed in such large and deep recess and so held in an upright position.

Figure 4:
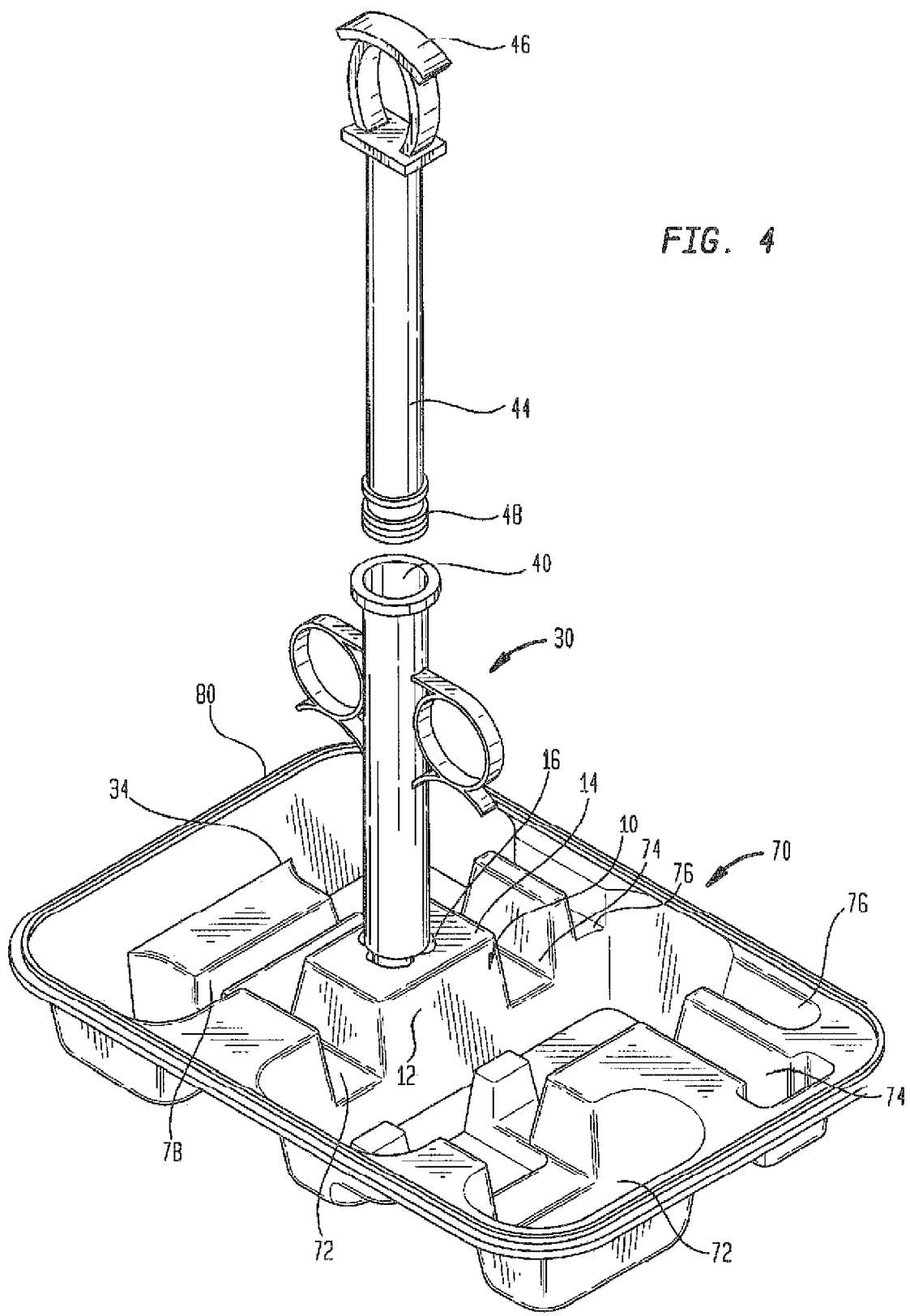
FIG. 4 is a perspective view of a syringe and a stand according to a further embodiment of the present invention.
Figure 6:
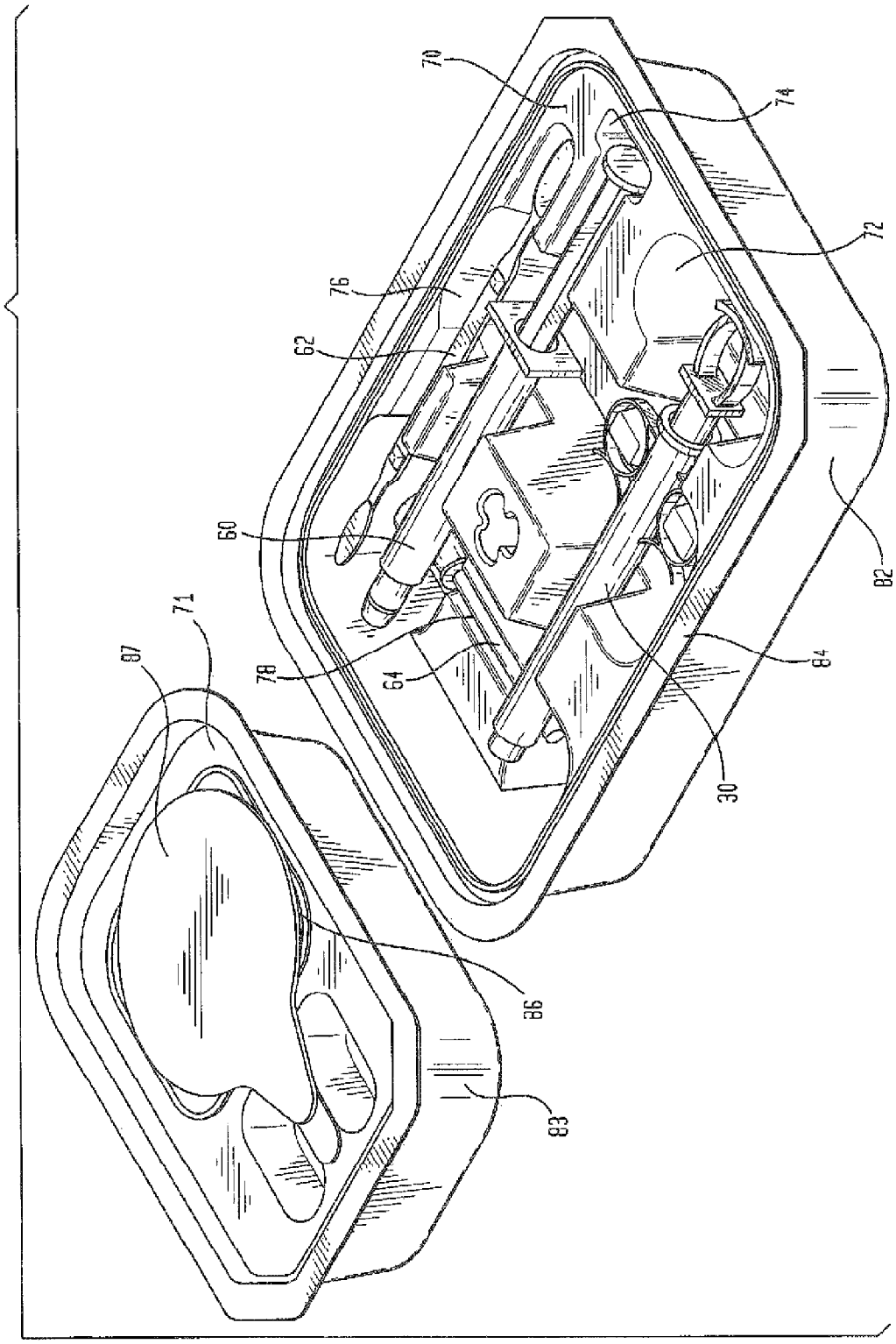
FIG. 6 is a perspective view of a kit including a syringe, a stand and components for use therewith according to an embodiment of the present invention.

Referring now to FIGS. 4-6, in a preferred embodiment of the present invention stand 10 is formed as part of package 70. Preferably package 70 is designed to carry syringe 30. More preferably, package 70 is one for a bone cement preparation kit. A kit according to this embodiment of the present invention is generally in the form of a blister pack in which stand 10 is connected to package 70 at base 12 of stand 10. Stand 10 can be located anywhere in package 70 but, for purposes of stability, is preferably located near the center of package 70. Package 70 has various compartments for the elements contained therein. Such elements include syringe 30 which is held within a snap channel 72 specifically designed to securely hold syringe 30 in a horizontal position within package 70. Preferably, package 70 also contains a compartment 74 designed to hold wet ingredient container 60, which is usually in the form of a second syringe. An additional compartment 76 is also preferably formed within package 70 and is dimensioned to securely hold a mixing spatula 62 therein. A fourth compartment 78 is preferably formed within package 70 such that it can hold a cannula 64 that is specifically adapted for attachment to nozzle 34 of syringe 30.

Additionally, mixing bowl 86 is preferably supplied with package 70. Mixing bowl 86 contains a dry ingredient which is part of a bone cement composition. Preferably, the wet ingredient is added to the dry ingredient in mixing bowl 86, and the two ingredients are mixed together using spatula 62 to form a bone cement composition.

As shown in FIG. 6, in a preferred embodiment of the current invention, package 70 is placed into an outer tray 82, which further helps to maintain the sterility of package 70 and the components held therein. A lid is then affixed to flange 84 of outer tray 82 to seal the components therein. Preferably, the lid is made from Tyvek™, or another material which serves the purpose of sealing the contents of package 70 so as to preserve the sterility and integrity of the ingredients. Although it is possible to supply mixing bowl 86 within package 70, having a corresponding compartment (not shown) formed therein, it is preferred that mixing bowl 86 is not included within package 70, but is otherwise supplied with package 70. Such an arrangement is shown in FIG. 6, wherein mixing bowl 86, having lid 87 affixed thereto, rests or is otherwise secured within a compartment formed in inner blister 71. Inner blister 71 is then placed in outer blister 83 and an outer lid (not shown) is affixed thereto. The assembled outer blister 83 and outer tray 82 are each sealed in their own outer pouch (not shown), which is preferably made of foil. Outer tray 82 and outer blister 83 are then inserted into a carton (not shown), which is typically made from cardboard or other similar material.

A desiccant is preferably included with mixing bowl 86, or any other container used to hold a dry ingredient of a bone cement composition used in connection with stand 10. The inclusion of a desiccant ensures that the storage environment of the powder is kept dry in order to prevent "aging" of the powder in the presence of free moisture, which would render the powder unusable. In the particular embodiment of the invention described with reference to FIG. 6, desiccant is included with mixing bowl 86 by placing a desiccant pack in outer blister 83 between outer blister 83 and inner blister 71. Preferably, a desiccant pack containing about 10 grams of color indicating silica gel is supplied, however other available desiccants include those made of clay and calcium chloride. The appropriate amount of desiccant varies with the particular application, the determination of which is generally understood in the art.

In certain applications of stand 10 including a package portion 70, it may be desired to provide package 70 without outer package 82. In such a case, package 70 includes an outer flange 80 to which a lid (not shown) is affixed.

Figure 7:
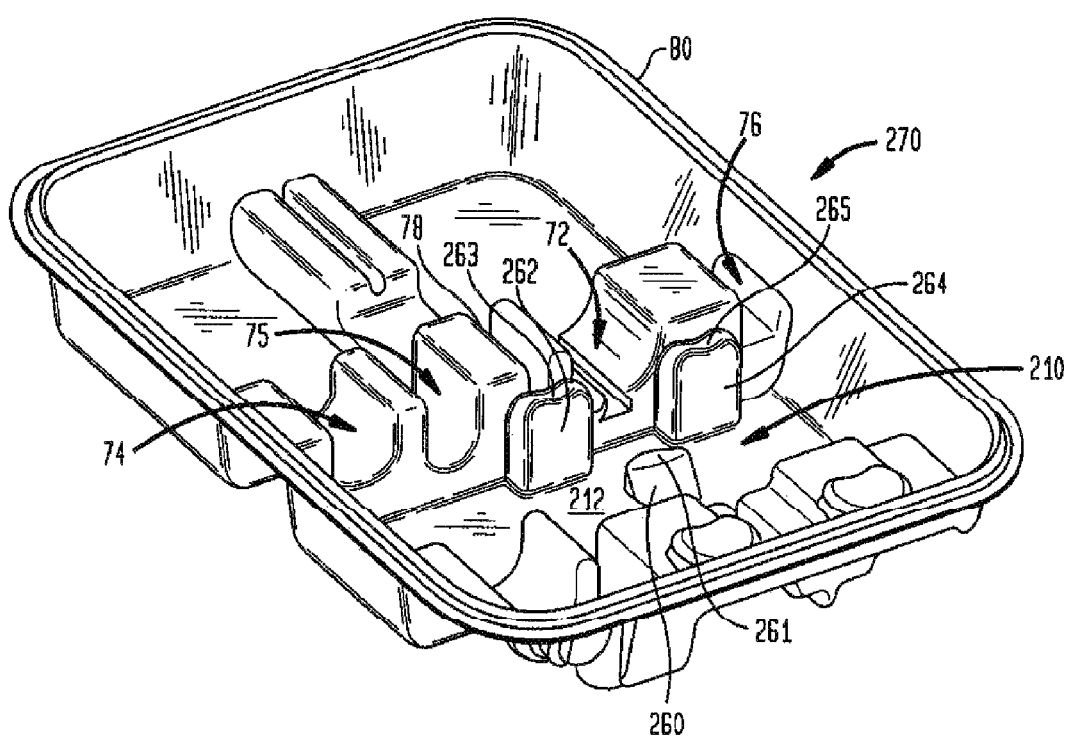
FIG. 7 is a perspective view of a stand according to an embodiment of the present invention.
Figure 8:
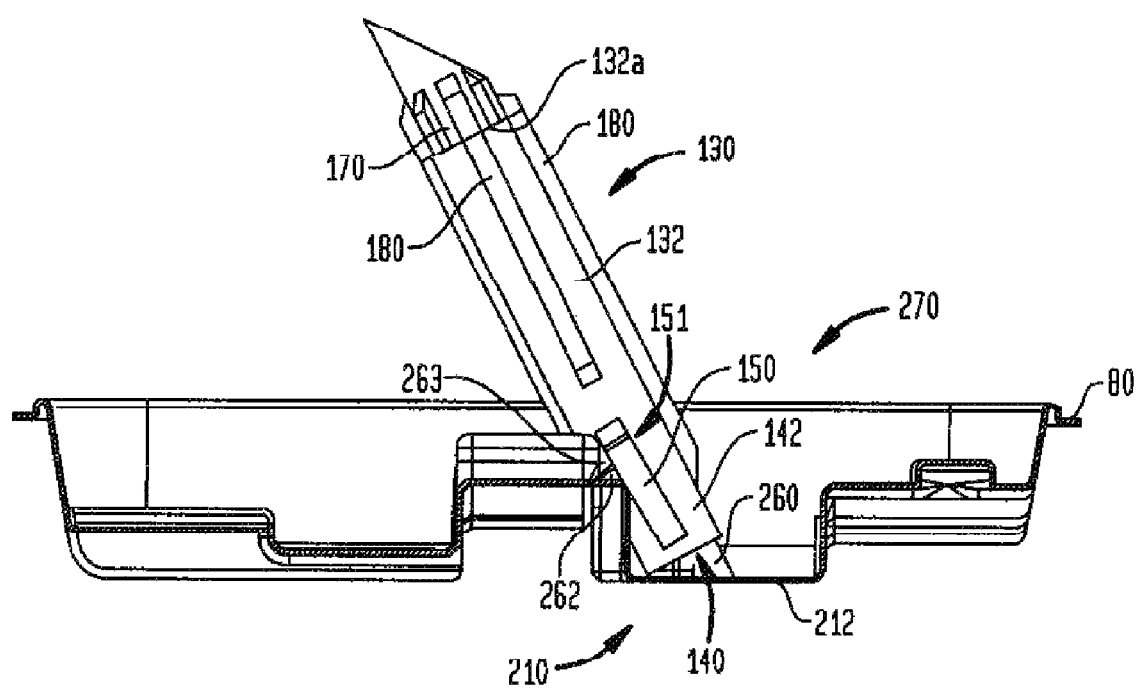
FIG. 8 is an elevational cross-section view of the stand shown in FIG. 7 holding a syringe according to an embodiment of the present invention.
Figure 9:
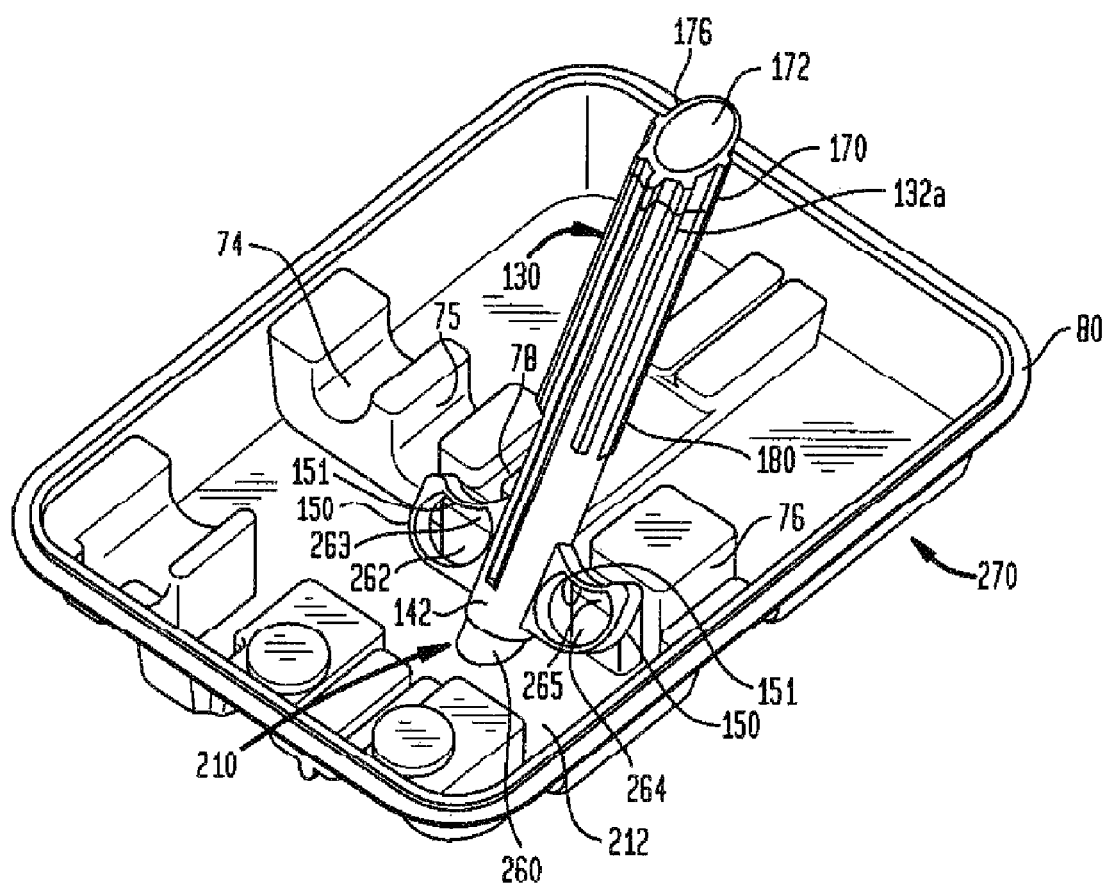
FIG. 9 is a perspective view of the stand and syringe shown in FIG. 7.

In an alternative embodiment shown in FIGS. 7-10, stand 210 includes a protrusion 260 extending generally upwardly from base 212. Protrusion 260 is structured to fit within the open end 140 of proximal end 142 of barrel 132 of syringe 130 (shown generally in FIG. 3). Although stand 210 is shown in FIGS. 7-9 as including a package portion 270 integrally formed with base 212, stand 210 may be formed so as to stand alone on a surface, supported by base 212, as shown and described with respect to previous embodiments discussed herein. Protrusion 260 may be shaped so as to form a pressure-fit within proximal end 142 of barrel 132. Additionally, protrusion 260 may be sufficiently sized and shaped so as to alone support syringe 130 in an upright position. Alternatively, as discussed below, protrusion 260 may act together with another structure of the tray and/or the syringe to support the syringe. The shape of the protrusion 260 in a preferred embodiment substantially matches the shape of at least a portion of the interior of barrel 132. For example, the syringe 130 depicted in the Figures has a substantially cylindrically-shaped barrel 132, and protrusion 260 has a substantially cylindrical shape so as to match that of barrel 132. However, any shape may be used for protrusion which accomplishes the desired fit between protrusion 260 and barrel 132. Also, a partially matching shape for protrusion 260 is contemplated.

Alternatively, stand 210 can further include a support that contacts a portion of barrel 132 located distally of proximal end 142. As shown in FIGS. 7-9, the support is in the form of a pair of pedestals 262, 264 that fit within handles 150 of syringe 130 (as best shown in FIG. 9). Pedestals 262, 264 each include a top surface 263, 265, which preferably are shaped to contact the uppermost portion 151 of the respective handles 150 such that handles 150 are supported by pedestals 262, 264. Preferably, top surfaces 263, 265 are contoured to match the shape of handles 150 of a syringe 130 provided therewith. For example, as shown in FIGS. 7-9, top surfaces 263, 265 are concave so as to match the particular shape of the handles 150 included on syringe 130 shown in FIGS. 9 and 10.

Figure 10:
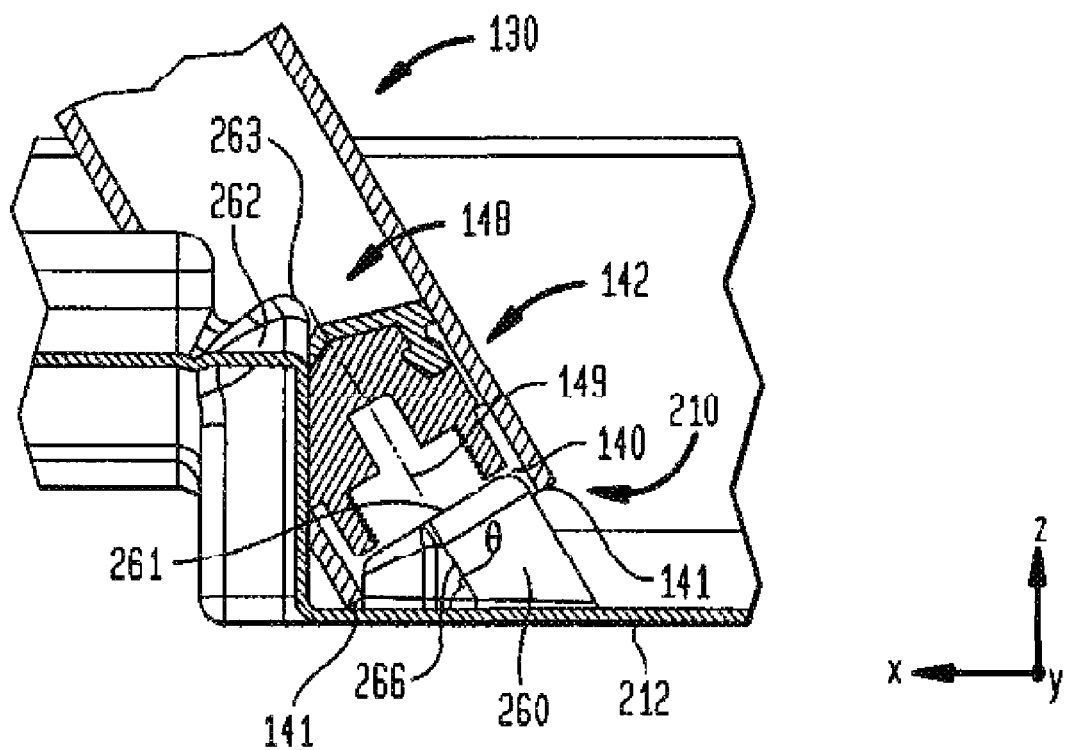
FIG. 10 is an elevational cross section view of a stand as shown in FIGS. 7 and 8 holding a syringe according to an embodiment of the present invention.

As shown in FIGS. 8-10, stand 210 preferably holds syringe 130 at an oblique angle relative to base 212. This may be accomplished by orienting protrusion 260 at an angle relative to base 212 that substantially matches the desired angle for syringe. Additionally, pedestals 262, 264 may be positioned so as to support syringe 130 at the desired angle. The proper position of top surfaces 263, 265 will depend on the location of handles 150 with respect to opening 140, and in particular with respect to lip 141 formed on the outside edge of opening 140, which may contact base 212 at a point along the intersection between base 212 and protrusion 260. Generally, to achieve the angled position of syringe 130 relative to base 212, top surfaces 263, and 265 will be spaced apart from protrusion in a lateral direction X and a vertical direction Z, as shown in FIG. 10. Preferably, syringe 130 is positioned at an angle θ relative to base 212 of between 40 and 70 degrees. More preferably, the angle θ between syringe 130 and base 212 is about 45 degrees. Additionally, as shown in FIG. 8, top surfaces 263, 264 may include a vertical surface, which may provide additional support for handles 150, particularly when stand 210 is structured to hold syringe 130 in an angled position.

Syringe 130 may be particularly adapted for use with the stand of the present embodiment. As discussed with respect to FIG. 3, syringe 130 includes an opening 152 at distal portion 132a of barrel 132, which provides for access to barrel 132 through which a material 88 can be poured. As shown in FIGS. 8 and 9, a funnel 170 can be adapted to be affixed to barrel 132 at the opening 152. Funnel 170 can include a threaded portion (not shown) that substantially matches that of threaded portion 133a included on distal end 132a of barrel 132. Funnel 170 can be of any suitable shape, but is preferably structured to provide an opening 172 having an area greater than open end 152. Additionally, funnel 170 can be used to provide an upwardly-angled edge 176 that may aide in pouring material 88 into syringe 130 when it is in an angled position.

Figure 11:
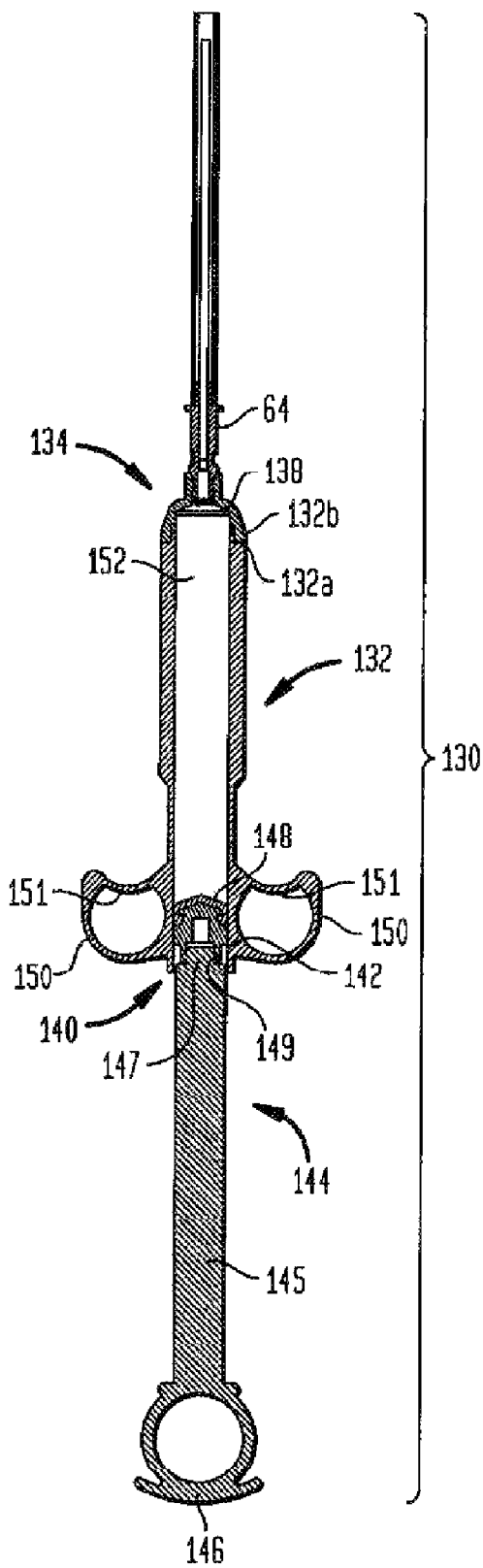
FIG. 11 is a cross section view of a syringe adapted for use with the stand such as that shown in FIGS. 7-10.

Furthermore, as shown in FIG. 11 plunger 144 may include rod 145 that is removable from tip 148. In such a structure, tip 148 is assembled within barrel 132 when syringe 130 is held on stand 210 so that material 88 is prevented from escaping through proximal end 142 of barrel 132 when syringe 130 is in the upright position shown in FIGS. 7-9 wherein proximal end 142 is vertically below distal end 132a. Tip 148 is preferably located within barrel 132 at a position which maximizes the amount of material that can be held therein, while allowing protrusion 260 to extend into barrel 132 at an appropriate distance. Accordingly, protrusion 260 may have a top surface 266 that contacts the proximal surface of the plunger tip 148 in order to help support tip 148 when material 88 is poured into syringe 130. When syringe 130 is not held in stand 210, plunger rod 145 can be assembled with tip 148 so that material 88 can be expelled from syringe 130 using plunger 144. In order to facilitate attachment between tip 148 and rod 145, tip may include, for example a threaded hole 149, and rod 145 may include a substantially mating threaded post 147 so that rod may be threaded and unthreaded from tip 148 as needed. Package portion 270 used with a syringe 130 of this type may include an additional chamber 75 that can be used to hold plunger rod 145 during transportation and storage of syringe 130.

Additionally, as shown in FIGS. 8 and 9, syringe 130 may include a plurality of ribs 180 spaced around and projecting from the outside surface 131 of barrel 132. Preferably, ribs 180 extend along barrel 130 in a proximal-distal direction, as shown; however, other arrangements are possible. Ribs 180 help space apart the hand of a user from barrel 132, should the user need to hold syringe 130 by barrel 132 during use. This is intended to reduce the amount of heat transferred from the hand of the user to material 88 contained within barrel 132, and is particularly advantageous when material 88 is a heat-activated composition. Preferably, between four and eight ribs 180 are included around outside surface 131 of barrel 132. Funnel 170 and/or nozzle 134 may also include ribs 180 which may additionally provide grip when attaching or removing these features from barrel 132 and may differentiate the features from barrel 132.

Figure 12:
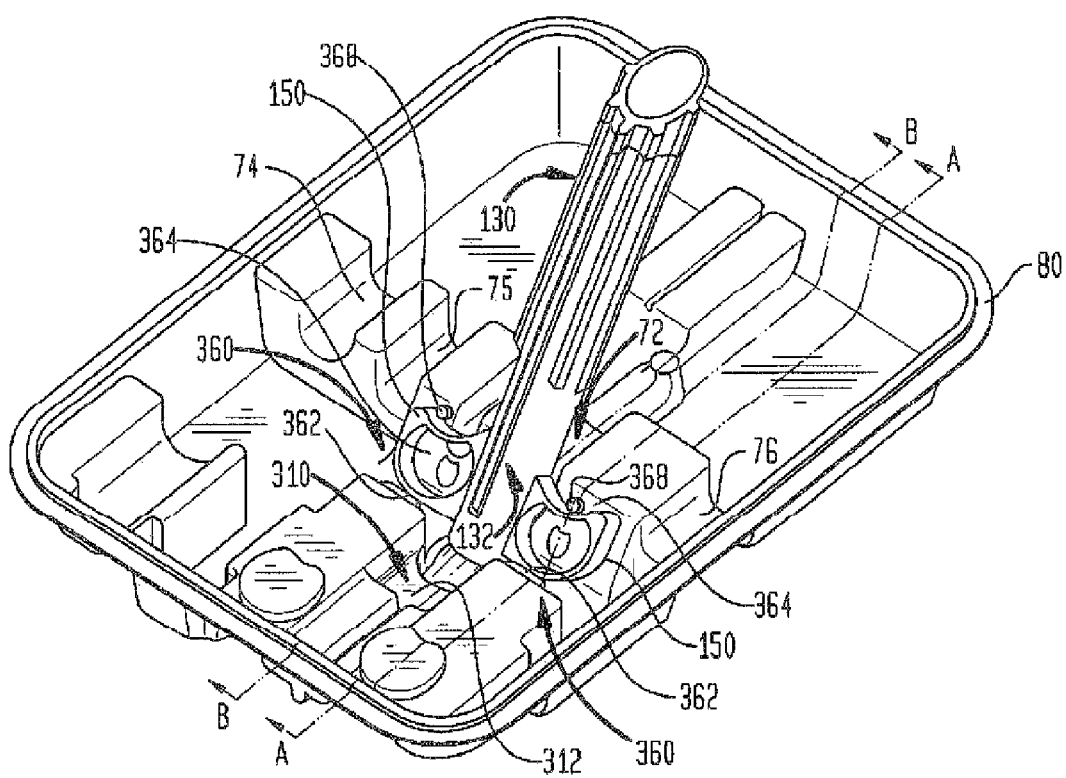
FIG. 12 is a perspective view of a syringe and a stand according to an alternative embodiment of the present invention.
Figure 13:
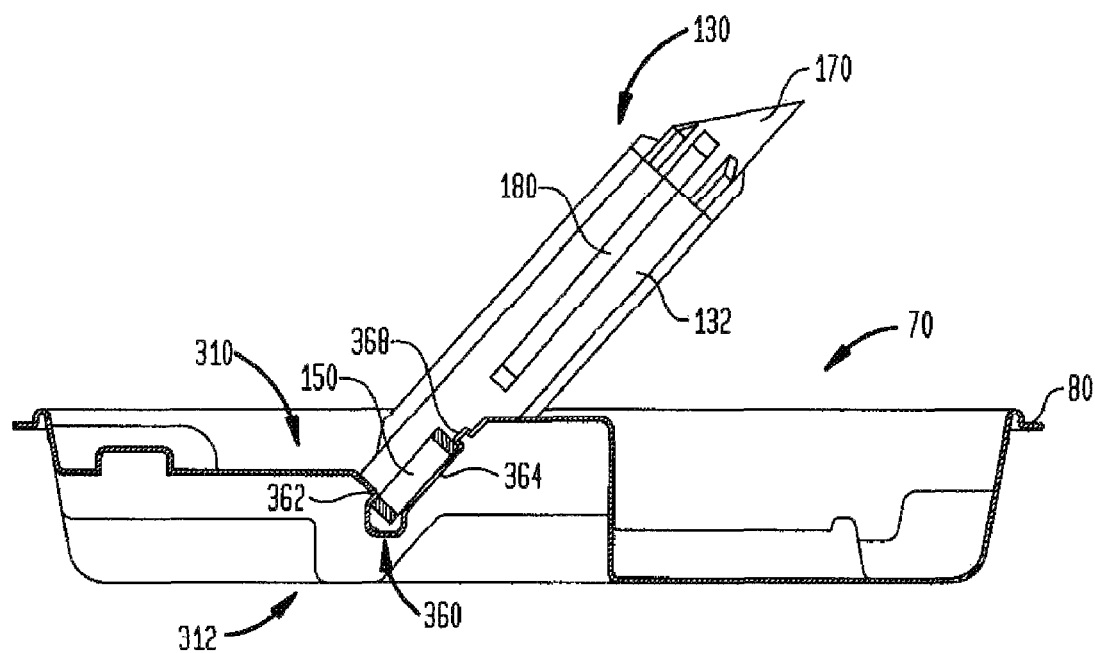
FIG. 13 is a cross-sectional view of the stand shown in FIG. 12 taken along line A-A with a syringe assembled therewith.

A further alternative embodiment of stand 310 for use with syringe 130 is shown in FIGS. 12-14. Stand 310 is similar to previous embodiments, except in the mechanism used to hold syringe 130. In particular, stand 310 uses a clip 360 in order to hold syringe 130 in the desired position. The exemplary embodiment of clip 360 shown in FIGS. 12-14 is structured so as to form a pressure fit at least on a portion of either or both handles 150 which project from the sides of barrel 132 of syringe 130. Other arrangements, however, are possible where clip 360 forms a pressure fit with other features or areas of syringe 130. Thus, for purposes of this disclosure, a "clip" is characterized by a structure that forms a pressure fit with an object or a portion of an object inserted therein in order to retain the object, wherein the pressure fit is achieved in a preferred embodiment, in part, through deformation of the structure. Preferably, such a structure may further act to retain an object by partially deforming into a maximum deformed position at an instance during insertion of the retained object into the clip and then by partially returning from the maximum deformed state when the object is fully inserted therein.

As shown in FIG. 12, clip 360 includes tab 362 and surface 364, wherein tab 362 contacts the proximal-most portion of handle 150. Surface 364 opposes the inside surface of tab 362 and is arranged to support handle 150 along a side thereof in order to maintain a position of syringe 130 relative to stand 310. For example, as shown in FIG. 12, surface 364 is positioned relative to base 312 of stand 310 at an angle of approximately 45 degrees, which acts to hold syringe 130 at an angle of approximately 45 degrees relative to base 312. Other angles for the position of surface 364 relative to base 312 are possible, including anywhere from 90 degrees to about 30 degrees, preferably between 30 degrees and 60 degrees, and more preferably about 45 degrees.

Indentation 366 may be formed in stand 310 so as to act with clip 360 in retaining syringe 130. As shown in FIG. 14, a portion of indentation 366 contacts a portion of barrel 132 of syringe 130, particularly at the proximal end of barrel 132. This contact between indentation 366 and the proximal end of barrel 132 furthers the retention of syringe 130 to stand 310 by providing an additional point of contact to make the angular position of syringe more stable and by furthering the pressure fit of clip 360 to syringe 130. The pressure fit is furthered, in the exemplary embodiment depicted in FIGS. 12-14, by creating leverage between the portion of syringe 130 that contacts the surface 364, namely handle 150, and the portion that contacts the indentation 366, namely the proximal end of barrel 132. In this arrangement, protrusion 362 provides the fulcrum for such leverage by providing a force to handle opposed to the force applied by surface 364 and indentation 366.

Surface 364 can include a bump 368, or other similar protrusion, extending therefrom. Bump 368 is positioned so as to abut the surface of handle 150 that faces away from clip. As shown in FIGS. 12-13, bump 368 abuts the distal-most surface of handle 150 and acts to partially prevent upward displacement of syringe 130 relative to stand 310.

As shown in FIG. 12, stand 310 preferably includes a pair of clips 360, each being sized and positioned to engage a respective one of the pair of handles 150 which project outwardly from barrel 132. The clips 360 are positioned such that one is on each side of indentation 366.

A further aspect of the present invention includes a method for using stand as discussed above. In one such embodiment, stand 10 according to FIG. 2 is provided as well as a syringe 30. Stand 10 is placed on a surface and syringe 30 is inserted into the stand. Stand 10 has an aperture 16 that secures syringe 10 at nozzle 34. Stand 10 is designed to maintain syringe 30 in an upright position. The injectable substance 88 is then deposited into the barrel 32 of syringe 30. This material can be anything that is intended to be injected using syringe 30 but is preferably an injectable bone cement composition. Plunger 44 is then inserted into barrel 32 of syringe 30. Syringe 30 is then removed from stand 10.

In a further embodiment of the present invention, a stand as discussed with reference to FIG. 4 is provided. Stand 10 includes a package portion 70 that includes compartment 72 for holding syringe 30 in a horizontal position therein during shipment or storage of stand 10. Preferably, package 70 contains additional compartments used to store other devices or containers used in connection with stand 10. Preferably, outer tray 82 has a lid (not shown) affixed thereto at flange 84 thereof. Lid is first removed from flange 84 and syringe 30 is removed from snap channel 72, where it is contained. Plunger 44 is then removed from barrel 32 of syringe 30 by pulling plunger 44 out of said barrel 32. Plunger 44 is then set aside and syringe 30 is inserted into stand 10 in an upright position. According to one preferred embodiment discussed above, nozzle 34 of syringe 30 is inserted into aperture 16 of stand 10. In an alternative embodiment, proximal end 146 of plunger 144 is inserted into aperture 116, which is appropriately formed therein.

In a preferred embodiment of the present invention, spatula 62 is included in compartment 76, which is preferably in the form of a snap-channel, within package 70, and a container 60 for a liquid ingredient is held compartment 74 within package 70. Both spatula 62 and container 60 are removed from package 70 and set aside. Preferably, mixing bowl 86, which contains a dry ingredient for a bone cement composition, is provided. Mixing bowl 86 contains lid 87 affixed thereto, which is removed and discarded. The liquid ingredient in container 60 is then deposited into mixing bowl 86, and spatula 62 is used to thoroughly mix the wet ingredient with the dry ingredient to form a bone cement composition. Once a homogeneous mixture is achieved from mixing of the wet and dry ingredients, mixing bowl 86 is placed near an appropriate opening of syringe 30, which will vary by application. If the nozzle 34 of syringe is inserted into aperture 16, this opening will be open end 40. Alternatively, if proximal end 146 of plunger 144 is inserted into aperture 116, then the mixing bowl will be placed near opening 152. Mixing bowl 86 is then tilted such that injectable substance 88 flows into barrel 32 of syringe 30. If necessary, spatula 62 is used to aid in this process.

Once the desired amount of the injectable substance 88 is transferred into syringe 30, plunger 44 is reinserted into barrel 32. In the embodiment of the present invention discussed with reference to FIG. 1, plunger 44 is advanced into the barrel 32 until tip 48 of the plunger 44 contacts the upper surface of the injectable substance 88 contained within syringe 30. To aid in this process, plunger 44 may include an air-release port (not shown) that begins at a small orifice in tip 48 of plunger 44 and continues to proximal end 46 of the plunger 44. This arrangement allows for any air in the syringe 30 above the surface of the injectable substance 88 to escape from inside syringe 30 without forcing the injectable substance 88 from syringe 30 through nozzle 34.

In a preferred embodiment of the present invention, package 70 further contains a cannula 64 held compartment 78. In this embodiment, cannula 64 is removed from compartment 78 and then syringe 30 is removed from stand 10. Cannula 64 is then assembled onto nozzle 34 of syringe 30. Incorporation of male and female thread portions aids in such assembly. This method allows for fast, efficient loading of a syringe 30 with an injectable substance 88 that is preferably a rapid-setting bone cement composition. It also allows for more accurate filling of syringe 30 by a single user.

Methods for using either stand 210 or stand 310 with syringe 130, as shown in FIGS. 7-10 and 12-14, respectively, are conducted in a similar manner as with respect to the methods discussed above. Additionally, funnel 170 would be removed from barrel 132 prior to assembling nozzle 134 thereto, and plunger rod 145 would be assembled to tip 148, which is positioned within barrel 132, after removal of syringe 130 from stand 210 or 310.

A stand according to the present invention is preferable regardless of whether or not the bone cement composition is heat-activated, because any fast setting bone cement composition must be quickly mixed and deposited into syringe 30 for injecting into a host before the bone cement composition sets. Furthermore, because bone cements and other additional materials are loaded from the top of the syringe, difficulty may be experienced by a single person attempting to fill syringe 30.

The syringe 30 referred to throughout can be of any type related to any field of use. In a preferred embodiment, syringe 30 relates to medical devices, and more particularly, to devices used in orthopedics, specifically delivery of rapid setting bone cement compositions. However, it is contemplated that variations of syringe 30, within other fields can be used in conjunction with the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A kit, comprising:
a syringe, including:
a barrel having a proximal portion and a distal portion, the proximal portion and the distal portion of the barrel being separable to provide an opening into the barrel of the syringe, the opening having a diameter substantially equal to a diameter of the barrel, wherein the proximal portion of the barrel has a proximal end and a distal end, the opening being located at the distal end;
a nozzle disposed on the distal portion of the barrel; and
a plunger slidably received within the proximal portion of the barrel;
a funnel adapted to be removably affixed to the proximal portion of the barrel at the opening, the funnel including a second opening larger than the opening in the barrel, and the funnel including an edge surrounding the second opening, the edge being generally aligned with a plane forming an oblique angle to a longitudinal axis of the syringe when the funnel is affixed to the proximal portion of the barrel; and
a stand adapted to support the proximal portion of the barrel in an orientation such that a vertical position of the distal end is maintained above a vertical position of the proximal end, wherein the orientation is an inclined orientation in which the longitudinal axis of the syringe is maintained at an inclined angle relative to a surface on which the stand is positioned.

2. The kit of claim 1, wherein the barrel includes a means for securing the proximal portion to the distal portion.

3. The kit of claim 2, wherein the means for securing the proximal portion to the distal portion includes a threaded connection.

4. The kit of claim 1, wherein the nozzle has an opening with a diameter smaller than the diameter of the barrel.

5. The kit of claim 1, wherein the proximal portion comprises a greater portion of the barrel than the distal portion.

6. The kit of claim 1, wherein the proximal portion of the barrel includes a handle.

7. The kit of claim 1, wherein the plunger includes:
a plunger tip slideably engaged within the barrel so as to form a seal between an interior wall of the barrel and an outer periphery of the plunger tip; and
a plunger rod removably affixed to the plunger tip.

8. The kit of claim 7, wherein the plunger rod is removably affixed to the plunger tip by a threaded connection.

9. The kit of claim 1, wherein the funnel includes a first threaded portion adapted to engage a second threaded portion on the proximal portion of barrel.

10. The kit of claim 9, wherein the distal portion of the barrel is securable to the proximal portion of the barrel by the second threaded portion on the proximal portion of the barrel.

11. The kit of claim 1, wherein the barrel of the syringe has an outer surface including a plurality of ribs extending outwardly therefrom.

12. The kit of claim 11, wherein each of the plurality of ribs are oriented along the longitudinal axis of the syringe.

13. The kit of claim 1, wherein the inclined angle is between 40 and 70 degrees.

14. The kit of claim 1, wherein the stand includes a base and a protrusion extending from the base, and wherein the protrusion is adapted to engage the proximal end of the proximal portion of the barrel, such that the engagement between the protrusion and the proximal end is sufficient to maintain the proximal portion in the inclined orientation.

15. The kit of claim 1, wherein the stand includes:
a base;
a protrusion extending from the base, the protrusion being adapted to engage the proximal end of the proximal portion of the barrel; and
a support on the base, the support being adapted to engage a location on the proximal portion barrel between the proximal and distal ends thereof;

wherein the engagement of the protrusion and the support with the proximal portion of the syringe barrel is adapted to maintain the proximal portion in the inclined orientation.

16. The kit of claim 1, wherein, when the funnel is affixed to the proximal portion of the barrel, the funnel and the barrel have substantially the same profile viewed along the longitudinal axis.

17. The kit of claim 1, wherein the barrel defines a substantially cylindrical shape along the longitudinal axis.

18. The kit of claim 17, wherein, when the funnel is affixed to the proximal portion of the barrel, the funnel continues the substantially cylindrical shape of the barrel along the longitudinal axis.

* * * * *

UNITED STATES PATENT AND TRADEMARK OFFICE
CERTIFICATE OF CORRECTION

PATENT NO.        : 8,303,599 B2                                Page 1 of 1
APPLICATION NO.   : 12/887663
DATED             : November 6, 2012
INVENTOR(S)       : Brian J. Hess and Matthew E. Murphy It is certified that error appears in the above-identified patent and that said Letters Patent is hereby corrected as shown below:

In the Specification
Column 2, line 24, after "within" insert --the--.
Column 2, line 28, after "includes" insert --a--.
Column 2, line 48, "are" should read --is--.
Column 2, line 52, after "surfaces" insert --of--.
Column 3, line 6, "being" should read --are--.
Column 3, line 42, "including" should read --includes--.
Column 3, line 61, after "that" insert --the--.
Column 4, line 3, "ht" should read --the--.
Column 4, line 53, after "includes" insert --a--.
Column 10, line 20, after "syringe" insert --130--.
Column 11, line 3, after "tip" insert --148--.
Column 11, line 5, after "rod" insert --145--.
Column 12, line 7, after "handle" insert --150--.
Column 12, line 11, after "clip" insert --360--.
Column 12, line 21, after "stand" insert --10--.
Column 12, line 25, "10 at nozzle 34" should read --30 at nozzle 34--.

In the Claims
Claim 9, column 14, line 43, after "of" insert --the--.
Claim 12, column 14, line 51, "are" should read --is--.
Claim 15, column 14, line 66, after "portion" insert --of the--.

Signed and Sealed this
Thirtieth Day of September, 2014

Michelle K. Lee
*Deputy Director of the United States Patent and Trademark Office*